United States Patent
Pezzuto et al.

(10) Patent No.: US 6,414,037 B1
(45) Date of Patent: Jul. 2, 2002

(54) PHARMACEUTICAL FORMULATIONS OF RESVERATROL AND METHODS OF USE THEREOF

(75) Inventors: John M. Pezzuto, River Forest, IL (US); Richard C. Moon, Plant City, FL (US); Mei-Shiang Jang, Chicago, IL (US); Aomar Ouali; Shengzhao Lin, both of Montreal (CA); Karla Slowing Barillas, Madrid (ES)

(73) Assignee: Pharmascience, Montreal (CA)

( * ) Notice: Subject to any disclaimer, the term of this patent is extended or adjusted under 35 U.S.C. 154(b) by 0 days.

(21) Appl. No.: 09/430,337

(22) Filed: Oct. 29, 1999

Related U.S. Application Data (63) Continuation-in-part of application No. 09/005,114, filed on Jan. 9, 1998, now Pat. No. 6,008,260.

(51) Int. Cl.$^7$ .............................................. A61K 31/05

(52) U.S. Cl. ........................ 514/733; 514/734; 514/736

(58) Field of Search ............................... 514/733, 736, 514/734

(56) References Cited

U.S. PATENT DOCUMENTS

| | | | |
|---|---|---|---|
| 5,411,986 A | 5/1995 | Cho et al. | 514/514 |
| 5,747,536 A | 5/1998 | Cavazza | 514/556 |
| 6,008,260 A | * 12/1999 | Pezzuto et al. | 514/733 |
| 6,080,701 A | * 6/2000 | Jeandet et al. | 514/2 |
| 6,132,740 A | * 10/2000 | Hu | 424/401 |

FOREIGN PATENT DOCUMENTS

| | | |
|---|---|---|
| JP | 61060609 | 3/1986 |
| JP | 409328410 A | * 12/1997 |
| JP | 10045566 | 2/1998 |
| WO | WO 99/04747 | 2/1999 |

OTHER PUBLICATIONS

Bertram (1979), "Reduction in the formation of carcinogen–induced transformed foci by penicillin G sodium in the C3H/10T.sub.1/2 CL8 cell line," *Cancer Lett.* 7:289–298.

Gerhauser et al. (1995), "Retinoids mediate potent cancer chemopreventive activity through transcriptional regulation of ornithine decarboxylase," *Nature Med.* 1(3)260–266.

Goodwin (1984), "Immunologic effects of nonsteroidal anti–inflammatory drugs," *Am. J. Med.* 77:7–15.

Jang et al. (1997) *Science* 275(5297):218–220 (Abstract Only).

Jayatilake et al. (1993), "Kinase inhibitors from polygonum cuspidatum," *J. Nat. Prod.* 56(10):1805–1810.

Kulmacz et al., "Cyclo–oxygenase: measurement, purification and properties," pp. 209–277, in *Prostaglandins and Related Substances*, IRL Press, Oxford (1987).

Landolph, "Chemical transformation in C3H 10T1/2 C18 mouse embryo fibroblasts: historical background, assessment of the transformation assay, and evolution and optimization of the transformation assay protocol," pp. 185–199, in *Transformation Assay of Established Cell Lines*, T. Kakunaga et al., eds., Oxford Univ. Press, Toronto (1985).

Mannilla et al. (1993), "Anti–leukaemic compounds derived from stilbenes in Picea abies bark," *Phytochemistry* 33:813–816.

Miura et al. (1997) *Igaku no Ayumi* 183(8):530–536 (Abstract Only).

Mondal et al. (1976), "Two–stage chemical oncogenesis in cultures of C3H/10T1/2 cells," *Cancer Res.* 36:2254–2260.

Moon et al., "Retinoid inhibition of experimental carcinogenesis," Chemistry and Biology of Retinoids, M.I. Dawson et al., eds., CRC Press, Boca Raton, FL, 501–518, 1990.

Plescia et al. (1975), "Subversion of immune system by tumor cells and role of prostaglandins," *Proc. Nat. Acad. Sci., USA* 72(5):1848–1851.

Prochaska et al. (1998), "Direct measurement of NAD(P)H:quinone reductase from cells cultured in microtiter wells: a screening assay for aniticarcinogenic enzyme inducers," *Anal. Biochem.* 169:328–336.

Reznikoff et al. (1973), "Quantitative and qualitative studies of chemical transformation of cloned C3H mouse embryo cells sensitive to postconfluence inhibition of cell division," *Cancer Res.* 33:3239–3249.

Sanders et al. (1997), *Book of Abstracts*, 214th ACS National Meeting, Am. Chem. Soc., Sep. 7, 1997.

Shamon et al. (1994), "A correlative approach for the identification of antimutagens that demonstrate chemopreventive activity," *Anticancer Res.* 14:1775–1778.

Sharma et al. (1994), "Screening of potential chemopreventive agents using biochemical markers of carcinogenesis," *Cancer Res.* 54:5848–5855.

Slowing et al. (1994), "Anti–inflammatory activity of leaf extracts of Eugenia jambos in rats," *J. of Ethnopharmacol.* 43:9–11.

Sporn et al. (1979), "Chemoprevention of cancer with retinoids," *Federation Proceedings* 38(11):2528–2534.

Suh et al. (1995), "Discovery of natural product chemopreventive agents utilizing HL–60 cell differentiation as a model," *Anticancer Res.* 15:233–240.

(List continued on next page.)

Primary Examiner—Zohreh Fay
Assistant Examiner—Brian-Yong Kwon
(74) *Attorney, Agent, or Firm*—Dianne E. Reed; J. Elin Hartrum; Reed & Associates (57) ABSTRACT

A method is provided for preventing or treating skin conditions, disorders or diseases, such as may be associated with or caused by inflammation, sun damage or natural aging. The method involves administration, preferably topical administration, of an active agent selected from the group consisting of resveratrol, pharmacologically acceptable salts, esters, amides, prodrugs and analogs thereof, and combinations of any of the foregoing. Pharmaceutical formulations for use in conjunction with the aforementioned method are provided as well.

37 Claims, 3 Drawing Sheets

OTHER PUBLICATIONS van der Ouderaa et al. (1982), "Purification of PGH synthase from sheep vesicular glands," *Methods Enzymol.* 86:60–68.

Wattenberg (1993), "Prevention–therapy–basic science and the resolution of the cancer problem: presidential address," *Cancer Research* 53:5890–5896.

Wild et al. (1987), "Prostaglandin H synthase–dependent mutagenic activation of heterocyclic aromatic amines of the IQ–type," *Carcinogenesis* 8(4):541–545.

Zenser et al. (1983), "Prostaglandin H synthase–catalyzed activation of benzidine: a model to assess pharmacologic intervention of the initiation of chemical carcinogenesis," *J. Pharmacol. Exp. Ther.* 227(3):545–550.

Zhang et al. (1994), "Anticarcinogenic activities of sulforaphane and structurally related synthetic norbornyl isothiocyanates," *Proc. Natl. Acad. Sci., USA* 91:3147–3150.

Jang et al. (1998), "Effects of Resveratrol on 12–O–Tetradecanoylphorbol–13–Acetate–Induced Oxidative Events and Gene Expression in Mouse Skin," *Cancer Letters* 134:81–89.

Subbaramaiah et al. (1998), "Resveratrol Inhibits the Expression of Cyclooxygenase-2 in Human Mammary and Oral Epithelial Cells," *Pharmaceutical Biology* 36:35–43.

* cited by examiner

○ 5μm TPA alone
□ 5μm TPA and
   1μm resveratrol
△ 5μm TPA and
   5μm reveratrol
▽ 5μm TPA and
   10μm resveratrol
◇ 5μm TPA and
   25μm resveratrol

PHARMACEUTICAL FORMULATIONS OF RESVERATROL AND METHODS OF USE THEREOF

CROSS-REFERENCE TO RELATED APPLICATIONS

This is a continuation-in-part of U.S. patent application Ser. No. 09/005,114, filed Jan. 9, 1998, now U.S. Pat. No. 6,008,260 the disclosure of which is incorporated by reference in its entirety.

ACKNOWLEDGEMENT OF GOVERNMENT SUPPORT

This invention was made with government support under Contract No. PO 1 CA48112 awarded by the National Cancer Institute. The United States Government has certain rights in this invention.

TECHNICAL FIELD

The present invention relates generally to pharmaceutical formulations and methods of use thereof, More particularly, the invention relates to pharmaceutical formulations of resveratrol (3,5,4'-trihydroxystilbene) that are useful, for example, in the prevention and treatment of skin conditions associated with inflammation, sun damage and aging. The invention finds utility in the fields of drug delivery, medicine and pharmacology.

BACKGROUND

It has been noted that there are a number of biologically active phenolic compounds present in wine, particularly red wine. Such compounds include, for example, catechin, epicatechin, quercetin, rutin, trans-resveratrol, cis-resveratrol, cis-resveratrol glucoside and trans-resveratrol glucoside. See, e.g., Goldberg et al. (1996) *Anal. Chem.* 68:1688–1694. These compounds have been shown to protect low-density lipoproteins against oxidation. The resveratrol isomers, in particular, have been found to promote vascular relaxation through the generation of nitric oxide by the endothelium, and to modulate eicosanoid synthesis in a manner that suggests use in preventing coronary heart disease. Id. at pp. 1688–89). This discovery appears to explain the studies demonstrating that moderate consumption of red wine tends to have a protective effect against heart disease. Bertelli et al. (1995) *Inst. J Tiss. Reac.* XVII(1):1–3.

trans-resveratrol quercetin cis-resveratrol rutin (+)-epicatechin (+)-catechin trans-resveratol glucoside cis-resveratol glucoside Resveratrol (3,5,4'-trihydroxystilbene) has been identified as a constituent not only of grape skins (Soleas et al. (1995) *Am. J. Enol. Vilic.* 46(3):346–352) but has also been found to be present in ground nuts, eucalyptus, and other plant species. Goldberg et al. (1995), *Am. J Enol. Vilic.* 46(2): 159–165. A great deal of interest has been focused on the compound's antifungal activity and its correlation with resistance to fungal infection. Id. at 159. Resveratrol may be obtained commercially (typically as the trans isomer, e.g. from the Sigma Chemical Company, St. Louis, Mo.), or it may be isolated from wine or grape skins, or it may be chemically synthesized. Synthesis is typically carried out by a Wittig reaction linking two substituted phenols through a styrene double bond, as described by Moreno-Manas et al. (1985) *Anal. Quim* 81:157–61 and subsequently modified by others (Jeandet et al. (1991) *Am. J. Enol. Vilic.* 42:41–46; Goldberg et al. (1994) *Anal. Chem.* 66: 3959–63).

There are more studies concerning trans-resveratrol than the cis isomer; however, the cis isomer appears to be equally important from a biological standpoint. Numerous uses have been proposed and evaluated for the resveratrol isomers. Jang et al. (1997) *Science* 275:218–220, show that resveratrol has cancer chemopreventive activity in assays representing three major stages of carcinogenesis.

That is, the authors found that the compound: (1) acted as an antioxidant and antimutagen and induced phase II drug-metabolizing enzymes; (2) mediated anti-inflammatory effects and inhibited cyclooxygenase and hydroperoxidase; and (3) induced human promyelocytic leukemia cell differentiation. In addition, as noted above, resveratrol has been extensively studied for its correlation to the cardiovascular utility of red wine. See, e.g., Bertelli et al., supra; Pace-Asciak et al. (1995), *Clinica Chimica Acta* 235:207–2191; and Frankel et al. (Apr. 24, 1993), *The Lancet* 341:1104. Neurologic uses have also been proposed (Lee et al. (1994), *Society for Neuroscience Abstracts* 20(1–2):1648).

To date, however, topical administration of resveratrol is unknown. The present invention is premised on the unexpected finding that topical administration of resveratrol is extremely effective in preventing or treating certain skin conditions, disorders and diseases, e.g., skin conditions associated with inflammation, skin damage associated with exposure to the sun, and the effects of natural aging. It has in addition been discovered that administration of resveratrol in the form of a microemulsion is a particularly effective mode of administering the active agent.

In addition, resveratrol has found to be useful as a cancer chemopreventive agent. Known cancer chemopreventive agents include nonsteroidal antiinflammatory drugs (NSAIDs) such as indomethacin, aspirin, piroxicam, and sulindac, all of which inhibit cyclooxygenase, abbreviated hereafter as COX. A COX inhibitory activity is important in cancer chemoprevention because COX catalyzes the conversion of arachidonic acid to proinflammatory substances, such as prostaglandins, which can stimulate tumor cell growth and suppress immune surveillance. Plescia et al. (1975) *Proc. Natl. Acad. Sci. U.S.A.* 72:1848; Goodwin (1984) *Am. J Med.* 77:7. In addition, COX can activate carcinogens to forms that damage genetic material. Zenser et al. (1983), *J. Pharmacol Exp. Ther.* 227:545; Wild et al. (1987) *Carcinogenesis* 8:541. Investigators have searched for new cancer chemopreventive agents by evaluating hundreds of plant extracts for a potential to inhibit COX. An extract derived from Cassia quinquatngilata Rich. (Leguminosae) was identified as a potent COX inhibitor, and on the basis of bioassay-guided fractionation, trans-resveratrol was identified as the active compound. See Mannila et al. (19983) *Phytochemistry* 33:813, and Jayatilake et al. (1993), *J. Nat. Prod.* 56:1805.

SUMMARY OF THE INVENTION

Accordingly, it is a primary object of the invention to address the above-mentioned needs in the art by providing a method for preventing or treating certain skin conditions, disorders and diseases.

It is another object of the invention to provide such a method by administering to a patient a formulation comprising an active agent selected from the group consisting of resveratrol, pharmacologically acceptable salts, esters, amides, prodrugs and analogs thereof, and combinations of any of the foregoing.

It is another object of the invention to provide such a method wherein the formulation is administered topically.

It is still another object of the invention to provide such a method wherein the skin condition, disorder or disease is associated with inflammation.

It is yet another object of the invention to provide such a method in the context of preventing or treating skin-related sun damage and/or the effects of natural aging on the skin.

It is an additional object of the invention to provide such a method in the context of preventing skin cancer.

It is a further object of the invention to provide such methods by administering resveratrol in stereoisomerically pure form, i.e., in either the cis or the trans form.

It is still a further object of the invention to provide novel pharmaceutical formulations comprising an active agent selected from the group consisting of resveratrol, pharmacologically acceptable salts, esters, amides, prodrugs and analogs thereof, and combinations of any of the foregoing, in combination with a pharmaceutically acceptable carrier.

Additional objects, advantages and novel features of the invention will be set forth in part in the description which follows, and in part will become apparent to those skilled in the art upon examination of the following, or may be learned by practice of the invention.

In one embodiment, then, a method is provided for preventing or treating certain skin conditions, disorders or diseases comprising administering to the susceptible or affected individual, preferably by application to the individual's skin, a pharmaceutical composition comprising a therapeutically effective amount of an active agent selected from the group consisting of resveratrol, pharmacologically acceptable salts, esters, amides, prodrugs and analogs thereof, and combinations of any of the foregoing. Generally, the active agent will be cis-resveratrol, trans-resveratrol, or a complex in which one or more of the compounds' hydroxyl groups are conjugated to a mono- or di-saccharide, e.g., cis-resveratrol glucoside, trans-resveratrol glucoside, etc. However, as will be appreciated by those skilled in the art, and as discussed in detail elsewhere herein, other forms of the active agents may also be used. The skin condition, disorder or disease may be, for example, psoriasis, contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer, effects of natural aging and the like.

In another embodiment, a pharmaceutical formulation is provided comprising an active agent as described above, with cis-resveratrol, trans-resveratrol, and conjugates of cis-resveratrol or trans-resveratrol with mono- or di-saccharides preferred. The formulation is preferably for topical administration, and thus also comprises a pharmaceutically acceptable topical carrier selected to correspond to the particular formulation type, e.g., ointment, lotion, cream, microemulsion, gel, oil, solution, or the like. The formulation may also contain one or more additional active agents and/or additives such as solubilizers, skin permeation enhancers, opacifiers, preservatives (e.g., anti-oxidants), gelling agents, buffering agents, surfactants, emulsifiers, emollients, thickening agents, stabilizers, humectants, colorants, fragrance, and the like. Inclusion of solubilizers and/or skin permeation enhancers is particularly preferred.

DETAILED DESCRIPTION OF THE INVENTION

OVERVIEW AND DEFINITIONS:

Before the present invention is described in detail, it is to be understood that unless otherwise indicated this invention is not limited to any particular formulation, carrier, or drug administration regimen, as such may vary. It is also to be understood that the terminology used herein is for the purpose of describing particular embodiments only and is not intended to limit the scope of the present invention.

(It must be noted that as used herein and in the claims, the singular forms "a," "and" and "the" include plural referents unless the context clearly dictates otherwise. Thus, for example, reference to "an active agent" in a formulation includes two or more active agents, reference to "a carrier" includes two or more carriers, and so forth.

In this specification and in the claims which follow, reference will be made to a number of terms which shall be defined to have the following meanings:

The term "topical administration" is used in its conventional sense to mean delivery of a topical drug or pharmacologically active agent to the skin or mucosa, as in, for example, the treatment of various skin disorders. In general, when the term "skin" is used herein, as in administration of a topical formulation to "the skin," it is to be understood that administration to mucosal tissue is intended as a possibility as well.

The terms "active agent," "drug" and "pharmacologically active agent" are used interchangeably herein to refer to a chemical material or compound that is suitable for topical administration and induces the desired physiological effect. The terms include derivatives, analogs and prodrugs of such compounds, as well as pharmaceutically acceptable salts, esters, amides, and the like.

The term "resveratrol" is intended to mean either the cis-isomer of resveratrol, the trans-isomer of resveratrol, or a mixture of the two isomers. The term is also intended to include both the naturally occurring active agent and the compound as it may be chemically synthesized in the laboratory. Further, when the term "resveratrol" is used herein, it is intended to encompass pharmacologically acceptable salts, esters, amides, prodrugs and analogs of resveratrol.

By the term "effective" or "therapeutically effective" amount of a drug is meant a nontoxic but sufficient amount of a compound, to provide the desired effect at a reasonable benefit/risk ratio attending any medical treatment. The desired effect and can be alleviation of the signs, symptoms, or causes of a disease, or any other desired alteration of a biological system.

The term "treat" as in "to treat a skin condition" is intended to include (1) preventing the condition, i.e., avoiding any clinical symptoms of the condition, (2) inhibiting the condition, that is, arresting the development or progression of clinical symptoms, and/or (3) relieving the condition, i.e., causing regression of clinical symptoms.

The terms "condition," "disorder" and "disease" are used interchangeably herein as referring to a physiological state that can be prevented or treated by administration of an active agent as described herein.

The term "individual" as in treatment of "an individual" is intended to refer to a mammalian individual afflicted with or prone to a condition, disorder or disease as specified herein, and includes both humans and animals.

By "pharmacologically acceptable" is meant a material that is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmacologically acceptable" salt or a "pharmacologically acceptable" ester of an active agent as provided herein is a salt or ester which is not biologically or otherwise undesirable.

"Penetration enhancer" or "permeation enhancer" as used herein relates to an increase in the permeability of the skin or mucosal tissue to the selected pharmacologically active agent, i.e., so that the rate at which the drug permeates through the skin or mucosa is increased.

"Optional" or "optionally" means that the subsequently described circumstance may or may not occur, so that the description includes instances where the circumstance occurs and instances where it does not. For example, recitation of an additive as "optionally present" in a formulation herein encompasses both the formulation containing the additive and the formulation not containing the additive.

ACTIVE AGENTS FOR TREATMENT:

The invention, as noted above, involves the administration of resveratrol to an individual in order to prevent or treat skin conditions associated with inflammation.

Resveratrol may be administered in natural form, i.e., as isolated from grape skins, wine or other plant-derived compositions, or it may be administered as chemically synthesized in the laboratory (e.g., using the methods of Moreno-Manas et al., Jeandet et al., or Goldberg et al. (1994), cited earlier herein), or as obtained commercially, e.g., from the Sigma Chemical Company (St. Louis, Mo.). Preferred methods for obtaining resveratrol from a natural source is to extract the compound from *P. capsudalum* or from the dried roots of *C. quinquangulata* which may be harvested in Peru. The dried ground plant material may be extracted with a suitable solvent, e.g., methanol, preferably followed by concentration and dilution with water. After washing with hexane or an equally suitable nonpolar organic solvent, the aqueous layer may be partitioned with, for example, ethyl acetate. The ethyl acetate extract is then separated into fractions using, for example, chloroform-methanol (0 to 30% methanol) as eluent over a silica gel chromatographic column. Fractions with higher concentrations of resveratrol may be combined and subjected to further column chromatography until the product is obtained in sufficiently high yield.

The active agent may be administered in the form of a pharmacologically acceptable salt, ester, amide, prodrug or analog or as a combination thereof. Salts, esters, amides, prodrugs and analogs of resveratrol may be prepared using standard procedures known to those skilled in the art of synthetic organic chemistry and pharmaceutical formulation, described, for example, by J. March, "Advanced Organic Chemistry: Reactions, Mechanisms and Structure," 4th Ed. (New York: Wiley-Interscience, 1992), and in Remington's Pharmaceutical Sciences, 19$^{th}$ Ed. (Easton, Pa.: Mack Publishing Company, 1995). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

Preferred derivatives of cis- and trans-resveratrol are those in which one or more of the compounds' hydroxyl groups, typically the 3-hydroxyl group, is conjugated to a mono- or di-saccharide, generally the 1-position of a monosaccharide. Examples of saccharides which may be conjugated to the resveratrol molecule include, but are not limited to, glucose, galactose, maltose, lactose and sucrose. Cis-resveratrol glucoside and trans-resveratrol glucoside are particularly preferred.

PHARMACEUTICAL FORMULATIONS:

In a preferred embodiment, the active agent is incorporated into a topical formulation containing a topical carrier that is generally suited to topical drug administration and comprising any such material known in the art. The topical carrier is selected so as to provide the composition in the desired form, e.g., as an ointment, lotion, cream, microemulsion, gel, oil, solution, or the like, and may be comprised of a material of either naturally occurring or synthetic origin. It is essential, clearly, that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Particularly preferred formulations herein are colorless, odorless ointments, lotions, creams, microemulsions and gels.

Ointments are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, cited in the preceding section, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols (PEGs) of varying molecular weight; again, reference may be had to Remington's, supra, for further information.

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. A particularly preferred lotion formulation for use in conjunction with the present invention contains propylene glycol mixed with a hydrophilic petrolatum such as that which may be obtained under the trademark Aquaphor® from Beiersdorf, Inc. (Norwalk, Conn.).

Creams containing the active agent are, as known in the art, viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Microemulsions are thermodynamically stable, isotropically clear dispersions of two immiscible liquids, such as oil and water, stabilized by an interfacial film of surfactant molecules (*Encyclopedia of Pharmaceutical Technology* (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Gel formulations are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2–10%), gelatin (at 2–15%), methylcellulose (at 3–5%), sodium carboxymethylcellulose (at 2–5%), carbomer (at 0.3–5%) or polyvinyl alcohol (at 10–20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in the topical formulations of the invention. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}MSO$) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; $C_2$–$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol®) and diethylene glycol monoethyl ether oleate (available commercially as Softcutol®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol®); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in the formulation, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In the preferred topical formulations of the invention, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

In an alternative embodiment, a pharmaceutical formulation is provided for oral or parenteral administration, in which case the formulation comprises a resveratrol-containing microemulsion as described above, but may contain alternative pharmaceutically acceptable carriers, vehicles, additives, etc. particularly suited to oral or parenteral drug administration. Alternatively, a resveratrol-containing microemulsion may be administered orally or parenterally substantially as described above, without modification.

UTILITY:

The pharmaceutical formulations of the invention are useful for treating humans and animals suffering from or prone to certain skin conditions, disorders or diseases associated with or caused by inflammation, sun damage or natural aging. For example, the compositions find utility in the prevention or treatment of psoriasis, contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer and the effects of natural aging. The formulations are administered topically, to the skin or mucosal tissue, as an ointment, lotion, cream, microemulsion, gel, solution or the like, as described in the preceding section, within the context of a dosing regimen effective to bring about the desired result. The preferred dose of active agent is in the range of about 0.005 to about 1 micromoles per kg per day, preferably about 0.05 to about 0.75 micromoles per kg per day, more typically about 0.075 to about 0.5 micromoles per kg per day. It will be recognized by those skilled in the art that the optimal quantity and spacing of individual dosages will be determined by the nature and extent of the condition being treated, the site of administration, and the particular individual undergoing treatment, and that such optimums can be determined by conventional techniques. That is, an optimal dosing regimen for any particular patient, i.e., the number and frequency of doses, can be ascertained using conventional course of treatment determination tests. Generally, a dosing regimen herein involves administration of the topical formulation at least once daily, and preferably one to four times daily, until symptoms have subsided.

The topical formulations of the invention can also be used as chemopreventive compositions. When used in a chemopreventive method, susceptible skin is treated prior to any visible condition in a particular individual.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains.

All patents, patent documents, and publications cited herein are hereby incorporated by reference in their entireties.

EXPERIMENTAL

The following examples are put forth so as to provide those of ordinary skill in the art with a complete disclosure and description of how to make and use the formulations of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All solvents, reagents and formulation components were of Pharmaceutical Grade.

EXAMPLE 1

Preparation of a Resveratrol Cream

A topical pharmaceutical composition containing trans-resveratrol was prepared in the form of a cream, as follows:

| Phase | Component | Wt. % |
|---|---|---|
| 1 | Polyethylene Glycol and Ethyleneglycol Palmitostearate | 5% |
|   | Caprilic/Capric Triglycerides | 5% |
|   | Oleoyl Macrogolglycerides (Labrafil M 1944CS) | 4% |
|   | Cetyl Alcohol | 5.5% |
|   | PPG-2 Myristyl Ether Propionate (Crodamol PMP) | 6% |
| 2 | Xanthan Gum | 0.3% |
|   | Purified Water | 48% |
| 3 | Propylene Glycol | 1% |
|   | Methylparaben | 0.18% |
|   | Propylparaben | 0.02% |
| 4 | Trans-Resveratrol | 10% |
|   | Diethylene Glycol Monoethyl Ether (Transcutol) | 15% |

The composition was prepared as follows. The xanthan gum was dispersed in water, and allowed to stand. Phase 1 (the oil phase) was heated to 75° C. Phase 2 was then heated to 75° C. Under high speed agitation, phase 1 was mixed into phase 2. The temperature was maintained at 75° C., and rapid stirring was continued for 10 min. The mixture was cooled slowly while stirring was continued at low speed. At 40° C., Phase 3 was added. The trans-resveratrol was then dispersed into diethylene glycol monoethyl ether, heated to 40° C., and then cooled down to 30° C. while stirring slowly (Phase 4). At 30° C., Phase 4 was added to the cream, mixed well, and cooled down to room temperature with slow mixing. An off-white, stable cream was obtained.

EXAMPLE 2

Micoremulsion of Resveratrol

A microemulsion of resveratrol was prepared having the following components:

| Component | Wt. % |
|---|---|
| Trans-Resveratrol | 10% |
| Diethylene Glycol Monoethyl Ether (Transcutol) | 47.4% |
| PEG-8 Caprylic/Capric Triglycerides (Labrasol) | 23.7% |
| Oleoyl Macrogolglycerides (Labrafil M 1944 CS) | 7.9% |
| PEG 400 | 4.7% |
| Water | 0.3% |

Trans-resveratrol was dispersed into diethylene glycol monoethyl ether. PEG-8 caprylic/capric glycerides and oleoyl macrogolglycerides were added, with agitation. PEG 400 was then slowly added, again, with agitation, followed by addition of water. A stable, transparent, slightly yellow microemulsion was obtained.

EXAMPLE 3

Inhibition of TPA-Induced Inflammation Test

Inhibition of inflammation induced by repeated application of 12-O-tetradecanoylphorbol-13-acetate (TPA) can be used to indicate the efficacy of various formulations used to treat inflammation. The test method is modified from that described by Marks et al. (1976) Cancer Res. 36:2636. TPA is known to induce changes in murine skin which mimic many of the inflammatory and epithelial changes which in occur in human skin diseases such as psoriasis. Thus, this mouse-based model is believed to be a good indicator of human response as well.

The composition of Example 1 (1 g, removing any excess) is initially applied to both ears of ten mice. The inflammatory stimulus (i.e., TPA) is then applied to the right ear of each mouse. Four hours later, edema is measured by weighing discs removed from the ear using a biopsy punch. A control group receives TPA in the right ear and the composition without the resveratrol to the left ear. The ratio of weight between discs receiving composition and TPA and TPA alone is calculated to give the percent inhibition of control swelling. The same process is carried out for the microemulsion of Example 2. The composition of Example 1 provides a 72% inhibition of swelling while the microemulsion of Example 2 provides a 74% inhibition of swelling as compared to the control. Thus, both formulations are shown to provide effective inhibition of inflammation.

EXAMPLE 4

Inhibition of Sunburn Cell Formation

The composition of Example 1 (1 g applied to 1 $cm^2$ area, removing any excess) is applied to the skin of mice. UV-B (100 $mJ/cm^2$) is irradiated onto the skin (health lamp SE20/SLE, Toshiba). Twenty four hours later, skin is biopsied at the treatment area and at a treatment-free area to serve as a control. The biopsied samples are stained using hematoxylin and eosin, after which the number of sunburn cells is counted under a microscope. The ratio of sunburn cells in areas receiving the treatment and in treatment-free areas is calculated to give the percent inhibition of sunburn cell formation. The same process is repeated using the microemulsion of Example 2. The composition of Example 1 is shown to provide 76% less sunburned cells and the microemulsion is shown to provide 79% less sunburned cells. Thus, both formulations are shown to provide effective inhibition of sunburn cell formation.

EXAMPLE 5

Inhibition of Wrinkle Formation in Hairless Mice

To each hairless mouse (HR/ICR, 6 weeks old), the composition of Example 1 (1 g applied to 1 $cm^2$ area, removing any excess) is applied. Approximately 10 minutes later, UV-B is irradiated unto the mouse using 6 bulbs of health lamps (SL20-SLE, Toshiba) so that the dose per irradiation is not greater than 1 MED (minimal erythema dose). Application of the formulation followed by irradiation is repeated five times per week over sixteen weeks. While the irradiation energy is measured using a UV-radiometer (UVR-305/S65D, Tokyo Optical K.K.) so that the dose per irradiation is not greater than 1 MED, energy is irradiated at an intensity of 0.28 $mW/cm^2$ with the total dose, 100 $mJ/cm^2$. As a control, a composition the same in all respects as the composition of Example 1 except lacking resveratrol is applied and the mouse is similarly irradiated following the protocol provided above. The same process is carried out for the microemulsion of Example 2.

The level of wrinkle formation is then visually determined using the following standards (wrinkle indices): (1) no wrinkle are formed; (2) small amounts of wrinkles are formed; (3) moderate amounts of wrinkles are formed; and (4) considerable amounts of wrinkles are formed.

In order to analyze the wrinkles, replicas of different skin areas (3 replicas per mouse) each having a round shape with a diameter of 1 cm are obtained using a hydrophilic exaflex, hydrophilic vinyl silicone imaging agent. Each replica is placed horizontally and lightened from an angle of 30°. The area of shadows formed by the wrinkles are analyzed as the area ratio using an image analyzing apparatus.

The results are shown below:

| Example | Wrinkle Index | Area ratio of image analysis (%) |
| --- | --- | --- |
| 1 | 2.06 | 3.01 |
| 2 | 1.97 | 2.85 |
| control | 3.78 | 6.46 |

Thus, both formulations are shown to inhibit wrinkle formation.

EXAMPLE 6

Prevention of Sun Damage in Humans

Once an MED (minimal erythema dose) is established for each of 10 patients, the composition of Example 1 is applied (under occlusion) to each patient 2 hours before UVB irradiation. Two areas of skin per patient are exposed to UVB irradiation: an area receiving the composition of Example 1 and an area receiving the same composition but without resveratrol. One hour after UVB irradiation, each patient has the same composition reapplied to the appropriate area of skin. For the next three days, each patient is evaluated and the irradiation sites are photographed. The results of the 10 patients are compiled and evaluated. The same process is followed for the microemulsion of Example 2. It is shown that resveratrol prevents sun damage in humans.

EXAMPLE 7

Topically Administered Resveratrol in Chemoprevention

Resveratrol was found to inhibit cellular events associated with tumor initiation, promotion, and progression. As discussed hereafter, the activity of resveratrol was demonstrated on the basis of ability of resveratrol to inhibit the cyclooxygenase activity of COX-1 (i.e., median effective dose $ED_{50}$ of 15 $\mu M$). This activity correlates with antitumor promotion. Although the inhibitory activity of resveratrol was less than that of some NSAIDs, such as indomethacin ($ED_{50}$=2.3 $\mu M$), the resveratrol activity was much greater than the activity of compounds such as aspirin ($ED_{50}$=880 $\mu M$). Also, unlike indomethacin and most other NSAIDs, resveratrol inhibited the hydroperoxidase activity of COX-1 ($ED_{50}$=3.7 $\mu M$).

Resveratrol-mediated inhibition was specific for the cyclooxygenase activity of COX-1 because there was no discernable activity when oxygen uptake was assessed with COX-2, an inducible form of the enzyme associated with responses such as inflammation, and inhibition of the hydroperoxidase activity of COX-2 ($ED_{50}$=85 $\mu M$) was greatly reduced relative to the activity observed with COX-1.

Figure 1:
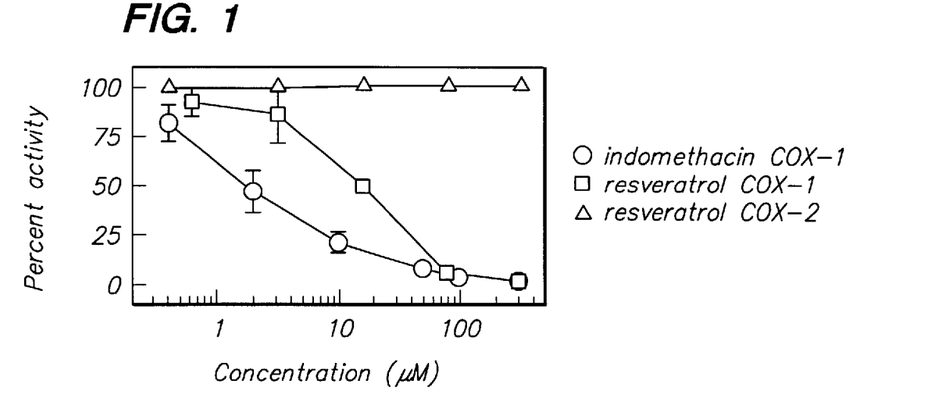
FIG. 1 contains plots of COX-1 and COX-2 activity vs. concentration of indomethacin and resveratrol.
Figure 2:
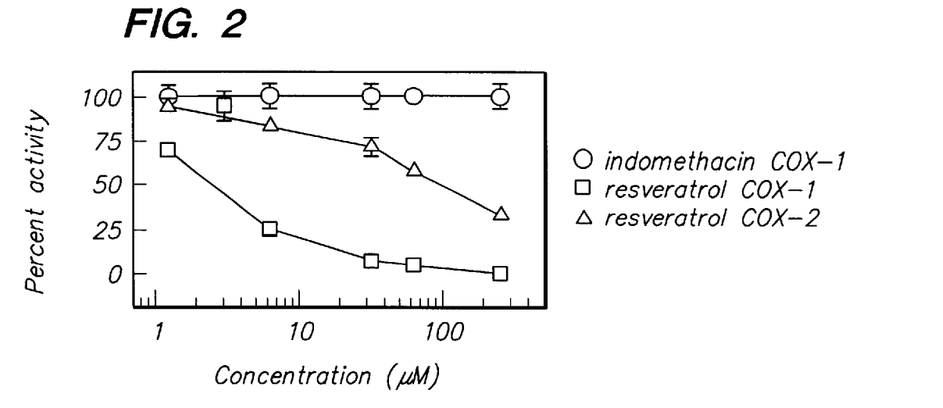
FIG. 2 contains plots of COX-1 and COX-2 hydroperoxidase activity vs. concentration of indomethacin and resveratrol.
Figure 3:
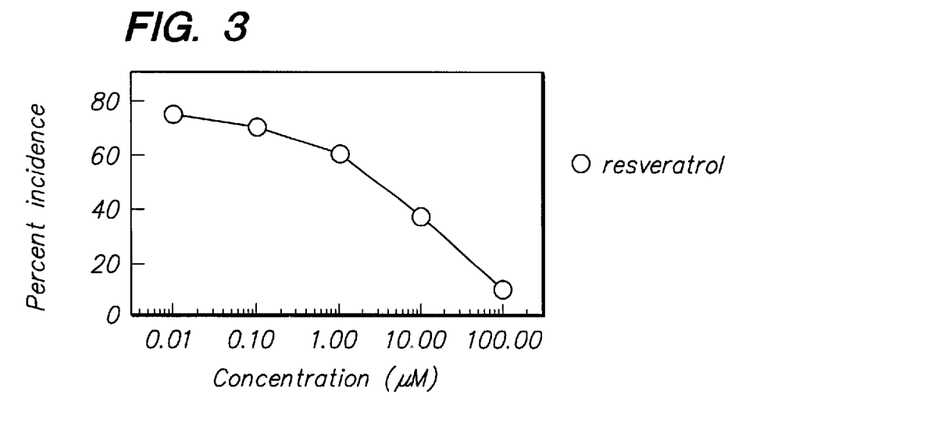
FIG. 3 is a plot of percent incidence of mouse mammary lesions vs. resveratrol concentration.

These results are illustrated in the plots of FIGS. 1–3. FIG. 1 shows the inhibitory effects of indomethacin on COX-1 and of resveratrol on COX-1 and COX-2. FIG. 1 contains plots of percent activity vs. concentration of indomethacin or resveratrol (in $\mu M$). COX activity was measured by measuring oxygen consumption at 37° C. The procedure is set forth in F. J. G. Van der Ouderaa et al., *Methods Enzymol*, 86, 60 (1982), and R. J. Kulmacz et al. in *Prostaglandins and Related Substances. A Practical Approach*, C. Benedetto et al., Eds. (IRL Press, Oxford, 1987), pp. 209–227, each incorporated herein by reference. The reactions were initiated by adding 0.6 mM arachidonic acid to a mixture containing 0.1M (molar) sodium phosphate (pH 7.4), 1.0 mM (millimolar) phenol, and 0.01 mM hemin; microsomes (0.2 mg of protein) derived from sheep seminal vesicles were used as a crude source of COX-1 or recombinant human COX-2 (0.1 mg of protein); and the test compound. FIG. 1 shows the dramatic inhibitory effect of resveratrol on COX-1.

FIG. 2 shows the inhibitory effect of indomethacin on COX-1 hydroperoxidase activity, and resveratrol on COX-1 or COX-2 hydroperoxidase activity. Hydroperoxidase activity was determined by spectrophotometry. The reaction mixtures contained 0.1M tris-NCl (pH 8.5), 1.2 $\mu M$ (micromolar) hemin, 0.24 mM, N,N,N',N'-tetramethyl-p-phenylenediamine (TMPD), COX-1 (36 $\mu g$ of protein) or COX-2 (45 $\mu g$ of protein), and a test compound. Hydrogen peroxide (250 $\mu M$) was used to initiate the reaction, and changes in absorbence at 595 nm (nanometers) were measured. Inhibitory activity was calculated by comparing the initial rate of change in absorbance in the presence of a test compound with that observed with dimethyl sulfoxide (DMSO) solvent only. Each point represents the mean of two replicate determinations. FIG. 2 shows that resveratrol strongly inhibits COX-1 hydroperoxidase activity.

FIG. 3 shows the inhibition of DMBA (7,12-dimethylbenz(a)anthracene)-induced preneoplastic lesions in mouse mammary gland culture by treatment with resveratrol. Mammary glands were incubated with resveratrol for 10 days and DMBA for 24 hours on day three. The procedure is set forth in Moon et al. in *Chemistry and Biology of Retinoids*, Eds. Dawson et al. (Boca Raton, Fla.: CRC Press, 1990), at pp. 501–518. Percent incidence of mammary lesions was determined after an additional 14 days of incubation. The data from resveratrol-treated groups was compared to control groups and the results expressed as a percentage. Resveratrol demonstrated an excellent ability to inhibit DMBA-induced preneoplastic lesions in mouse mammary gland cultures.

Based on the results illustrated in FIGS. 1–3, the antiinflammatory activity of resveratrol was investigated. In a carrageenan-induced model of inflammation in rats, resveratrol significantly reduced pedal edema both in the acute phase (3 to 7 hours) and in the chronic phase (24 to 144 hours). The edema-suppressing activity of resveratrol was greater than that of phenylbutazone, and was similar to that of indomethacin. These data are set forth in FIG. 4. Overall, the data in FIG. 4 demonstrates the ability of resveratrol to inhibit tumor promotion.

Figure 4:
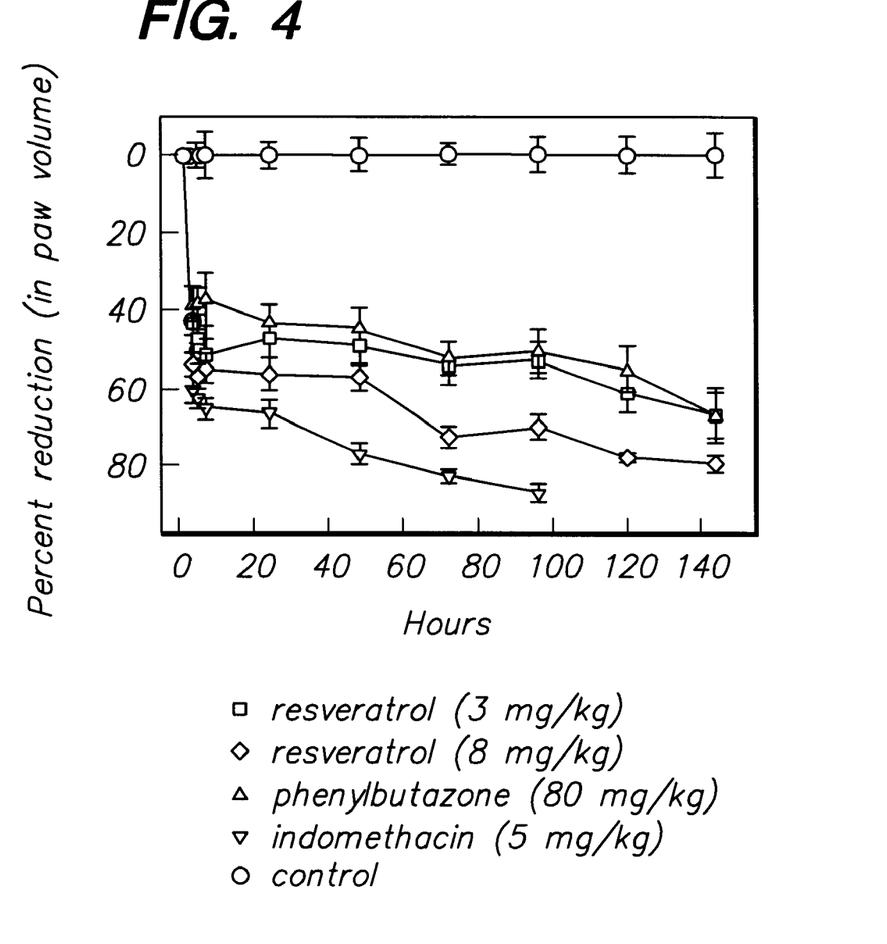
FIG. 4 contains plots of percent reduction in paw volume vs. time (hours) for carrageenan-induced inflammation in rats for various drugs vs. a control group.

In particular, FIG. 4 shows the effects of resveratrol (at 3 mg/kg and 8 mg/kg of body weight), phenylbutazone, and indomethacin on carrageenan-induced inflammation in rats. The procedure is set forth in Slowing et al. (1994) *J. Ethnopharmacol.* 43:9 (1994), incorporated herein by reference. In these tests, female Wistar rats (150 to 200 g body weight) were divided into groups of seven animals each. All rats received 0.1 ml of Freund's complete adjuvant, available from Sigma Chemical Co., St. Louis, Mo., by intradermal injection into the tail. Animals were used 7 days after injection of adjuvant. One hour after oral administration of resveratrol (3 or 8 mg per kilogram of body weight) or reference drugs including phenylbutazone (80 mg/kg) and indomethacin (5 mg/kg), the rats were injected with 0.1 ml of a 2% (w/v) suspension of carrageenan in saline solution into the left hind paw. For the control group, a 1:1 mixture of Tween 80 (i.e., polysorbate 80, available from ICI Americas, Inc., Wilmington, Del.) and water (0.2/3.3, v/v) and 1% (w/v) methylcellulose was used as a vehicle. The left hind paw volume of each rat was measured by water plethysmography on a Letica, Model L17500, before the adjuvant injection, and, again, 6 days later, before the injection of carrageenan. Paw volumes were determined within 3 to 144 hours after injection of carrageenan. Inhibition of edema was calculated relative to the mean edema of the vehicle-treated control group.

Percent reduction was determined by comparing the paw volume of rats in the control group (treated with carrageenan only) to paw volume of rats in the drug-treated group. Dosing was repeated daily for 7 days. Hours refers to hours after carrageenan injection. The data for the indomethacin group at 120 hours and 140 hours were not reliable because of the induction of secondary lesions. The plots in FIG. 4 show that resveratrol was effective in reducing carrageenan-induced inflammation in rats.

Resveratrol also was found to inhibit events associated with tumor initiation. For example, resveratrol inhibited free-radical formation ($ED_{50}$=27 $\mu$M), in a dose-dependent manner, when human promyelocytic leukemia (HL-60) cells were treated with TPA. The procedure is set forth in Sharma et al. (1994) *Cancer Res.* 54:5848. In these tests, HL-60 cells were maintained in RPMI 1640 medium (available from Gibco BRL, Grand Island, N.Y.) supplemented with 5% heat-inactivated calf serum, penicillin G sodium (100 U/ml), and streptomycin sulphate (100 $\mu$/ml) (Gibco BRL) at 37° C. in a humidified atmosphere at 5% carbon dioxide in air. Differentiation was induced by a 7-day treatment with 1.3% DMSO, and the cells were cultured in 96-well plates (1×10$^6$ cells per well) in Hanks' balanced salt solution containing 30 mM Hepes, pH 7.6. After the addition of TPA (8 $\mu$M) to induce free radical formation, cytochrome c (160 $\mu$M) and resveratrol were added. The cells were incubated for 1 hour at 37° C., and antioxidant activity was determined by monitoring absorbance at 550 nm. The same reaction mixture, but lacking the HL-60 cells, was used as a blank control.

Resveratrol also functioned as an antimutagen, as illustrated by a dose-dependent inhibition of the mutagenic response induced by treatment of *Salmonella typhimurium* strain TM677 with 7,12-dimethyl-benz(a)anthracene (DMBA) ($ED_{50}$=4 $\mu$M). This procedure is set forth in Shamon et al. (1995) *Anticancer Res*, 14:1775 (1995), incorporated herein by reference. In these tests, a reaction mixture was prepared containing *Salmonella typhimurium* strain TM677, S9 liver homogenate derived from Aroclor 1254-pretreated rats, a NADPH-generating system (NADPH is the reduced form of nicotinamide adenine dinucleotide phosphate), and various concentrations of resveratrol, which were added one minute before the addition of 80 $\mu$M DMBA. After incubation for 2 hours at 37° C., the bacteria were recovered by centrifugation, resuspended, and plated (in triplicate) on minimal agar in the presence or absence of 8-azaguanine. The plates then were incubated for 48 hours at 37° C., and the results were expressed as mutant fractions, i.e., the average number of colonies capable of growing in the presence of 8-azaguanine divided by the average number of colonies capable of growing in the absence of 8-azaguanine, after correcting for dilution factors. The percent inhibition was calculated relative to control plates that were treated with DMSO only.

In addition, resveratrol induced quinone reductase activity with cultured mouse hepatoma (Hepa 1c1c7) cells (concentration required to double activity, 21 $\mu$M). See Prochaska et al. (1988) *Anal. Biochem.* 169:328. This result is important because phase II enzymes, such as quinone reductase, are capable of metabolically detoxifying carcinogens. See Zhang et al. (1994), *Proc. Nail. Acad. Sci., U.S.A.* 91:3247. An identical response profile was observed with cultured BP$^1$Cl hepatoma cells (a derivative of Hepa 1c1c7 cells that is incapable of phase I enzyme induction), indicating that resveratrol is a monofunctional inducer.

In addition, the ability of resveratrol to inhibit the progression stage of carcinogenesis was tested by treating cultured HL-60 cells with resveratrol. See Suh et al. (1995) *Anticaucer Res.* 15:233. Under normal culture conditions, these cells have unlimited proliferative capacity. In a dose-dependent manner, resveratrol-induced expression of nitroblue tetrazolium reduction activity, a marker of granulocyte formation ($ED_{50}$=11 $\mu$M), and nonspecific acid esterase activity, a marker of macrophase (monocyte) formation ($ED_{50}$=19 $\mu$M). Concurrently, incorporation of [$^3$H] thymidine was inhibited ($ED_{50}$=18 $\mu$M), which is indicative of terminal differentiation to a nonproliferative phenotype.

In order to more directly assess the cancer chemopreventive activity of resveratrol, the effects of resveratrol in a mouse mammary gland culture model of carcinogenesis was investigated. Resveratrol inhibited, in a dose-dependent manner, the development of DMBA-induced preneoplastic lesions ($ED_{50}$=3.1 μM) (see FIG. 3). No signs of toxicity were observed, as judged by morphological examination of the glands.

In addition, tumorigenesis in the two-stage mouse skin cancer model in which DMBA was used as initiator and TPA as promoter was studied. During an 18-week study, mice treated with DMBA-plus TPA developed an average of two tumors per mouse with 40% tumor incidence, as illustrated in FIG. 5(a).

Figure 5A:
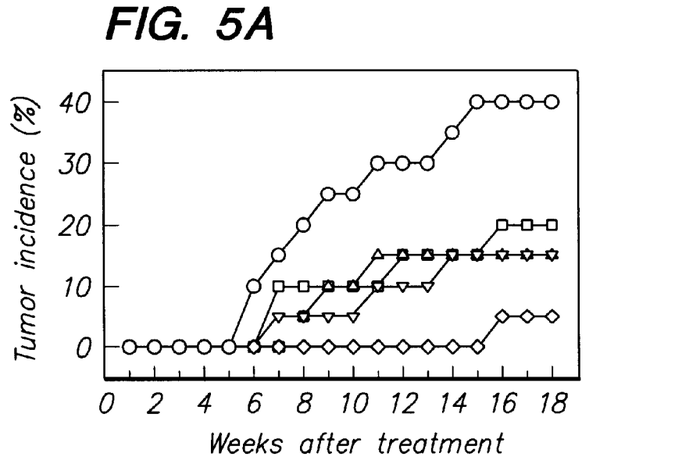
FIG. 5 contains plots of % tumor incidence (a) and number of tumors (b) vs. time after resveratrol treatment.
Figure 5B:
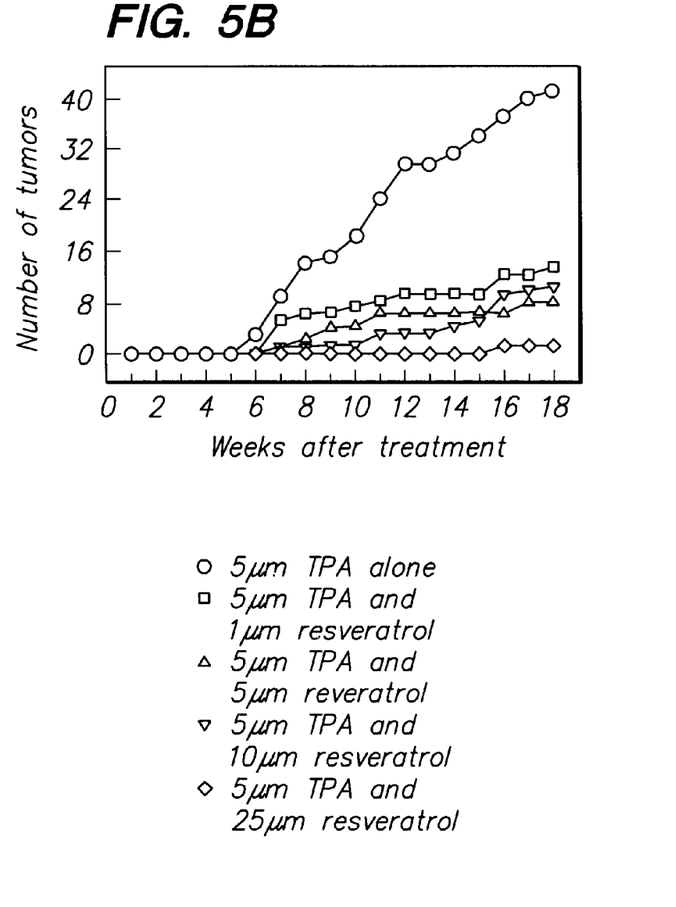

In particular, FIG. 5 shows the effect of resveratrol on tumorigenesis in the two-stage mouse skin model. Six groups of 20 female CD-1 mice (4 to 5 weeks old) were treated topically with 200 μmol of DMBA in 0.2 ml of acetone on the shaved dorsal region. See Gerhauser et al. (1995) Nature Med. 1:260 (1995). One week later, the mice were treated with 5 μmol of TPA in 0.2 ml of acetone alone or together with 1, 5, 10, or 25 μmol of resveratrol in 0.2 ml of acetone, twice a week for 18 weeks. Animals were weighed weekly and observed for tumor development once every week. FIG. 5A shows percent incidence of observable skin tumors. FIG. 5B shows total number of observable skin tumors. Overall, FIG. 5 shows that resveratrol greatly reduced the incidence of tumors in the mouse skin model.

Application of 1, 5, 10, or 25 μmol of resveratrol, together with TPA twice a week for 18 weeks, reduced the number of skin tumors per mouse by 68, 81, 76, and 98%, respectively, and the percentage of mice with tumors was lowered by 50, 63, 63, and 88%, respectively (FIG. 5(b)). No overt signs of resveratrol-induced toxicity were observed, as judged by visual inspection of the skin, gross morphological examination of major organ systems, or change in body weights, relative to controls.

To further demonstrate the ability of resveratrol to act as a cancer chemopreventive agent, tests were performed to determine whether resveratrol possesses activity against chemically induced neoplastic transformation in the C3H/10T1/2 clone 8 cells. This 10T1/2 cell line of mouse embryo fibroblasts has been widely used as an experimental system to study neoplastic transformation induced by a variety of agents, such as polycyclic hydrocarbons, methylating agents, and X-rays. Two-stage transformation assays, with 3-methylcholanthrene (MCA) or DMBA as inducer and TPA as promoter, were performed in these tests.

C3H10T1/2 Cl 8 cells were purchased from the American Type Culture Collection (ATCC CCL 226, Rockville, Md.) and maintained in Eagle's basal medium with Earle's salts (EBME) containing 10% (v/v) fetal bovine serum (FBS, Gibco Laboratories, Chagrin Falls, Ohio) without antibiotics, and sodium bicarbonate (2.2 gl). Cells were seeded at $5\times10^4$ per 75 $cm^2$ flask and grown in a humidified incubator containing 5% carbon dioxide in air at 37° C. Cells used in all these experiments were passage between 10–13.

Two-stage transformation assays in C3H10T1/2 cells were performed according to a procedure modified from that described in Mondal et al. (1976) Cancer Res. 36:2254–2260. One thousand cells obtained from freshly confluent flasks were seeded per well in 12-well plate containing 2 ml of medium (12 wells per experimental point). After incubation at 37° C. for three days, MCA or DMBA (2 mg/ml stock solution in DMSO) was added to give final concentrations of 0.25 μg/ml. Carcinogen-containing medium was removed from the growing cultures after 24 hours and cells were rinsed once with PBS before addition of fresh EBME supplemented with 10% FBS and gentamycin (25 μg/ml). Following five days of further incubation without carcinogen, medium was changed to fresh medium containing TPA (0.1 μg/ml) or TPA and different concentrations of resveratrol. TPA and test compounds were added to the medium each time the medium was changed. Medium was changed on all plates twice weekly. After confluency was reached, the FBS concentration was reduced to 5% and amphotericin B (fungizone, 1.5 μg/ml) was added to the medium (see Reznikoff et al. (1973) Cancer Res. 33:3239–3249 and Bertram (1979) Cancer Lett. 7:289–298). Subsequent medium changes were performed weekly. Cultures were fixed with methanol and stained with Giemsa at the seventh week. Type II and III transformed foci were scored according to the teachings of Landolph "Transformation Assay of Established Cell Lines: Mechanism and Application," Eds. Kakunaga et al. (Toronto: Oxford University Press, 1985), at pp. 185–199.

Table 1 summarizes the effects of various cancer chemopreventive agents, including resveratrol, on chemical-induced neoplastic transformation.

TABLE 1

Effects of various chemopreventive agents on chemical-induced neoplastic transformation

| Treatment | Total No. type II | Total No. type III | Total No. of foci/no. wells scored | No. of wells foci/total no. of wells | Wells with foci (%) |
|---|---|---|---|---|---|
| 0.5% DMSO control | 0 | 0 | 0/12 | 0/12 | 0 |
| MCA (5.0)* | 9 | 2 | 11/12 | 8/12 | 67 |
| MCA (0.25) | 0 | 0 | 0/12 | 0/12 | 0 |
| MCA (0.25); TPA (0.1) | 8 | 0 | 8/12 | 7/12 | 58 |
| MCA (0.25); TPA (0.1); resveratrol 2.5 μM | 3 | 0 | 3/12 | 2/12 | 17 |
| MCA (0.25); TPA (0.1); resveratrol 5.0 μM | 3 | 1 | 4/12 | 2/12 | 17 |
| 0.5% DMSO | 0 | 0 | 0/12 | 0/12 | 0 |
| MCA (0.25); TPA (0.1); resveratrol 10 | 1 | 0 | 1/12 | 1/12 | 8.3 |
| 0.5% DMSO control | 0 | 0 | 0/12 | 0/12 | 0 |
| DMBA (5.0) | 4 | 0 | 4/12 | 2/12 | 17 |
| DMBA (0.25) | 1 | 0 | 1/12 | 1/12 | 8.3 |
| DMBA (0.25); TPA (0.1) | 4 | 0 | 4/12 | 4/12 | 33 |
| DMBA (0.25); TPA (0.1); resveratrol 2.5 | 3 | 0 | 3/12 | 3/12 | 25 |
| DMBA (0.25); TPA (0.1); resveratrol 5.0 | 1 | 1 | 2/12 | 2/12 | 17 |
| 0.5% DMSO control | 0 | 0 | 0/12 | 0/12 | 0 |
| DMBA (0.25); TPA (0.1); resveratrol 10 μM | 1 | 1 | 2/12 | 2/12 | 17 |
| DMBA (0.25); TPA (0.1); aspirin 200 μM | 0 | 0 | 0/12 | 0/12 | 0 |
| DMBA (0.25); TPA (0.1); all-trans-retinyl acetate (0.3) | 0 | 0 | 0/12 | 0/12 | 0 |

TABLE 1-continued

Effects of various chemopreventive agents on chemical-induced neoplastic transformation

| Treatment | Total No. type II | Total No. type III | Total No. of foci/no. wells scored | No. of wells foci/total no. of wells | Wells with foci (%) |
|---|---|---|---|---|---|
| DMBA (0.25); TPA (0.1); Vit E. 100 μM | 4 | 0 | 4/12 | 4/12 | 33 |

*Numbers in parenthesis, concentration (μg/ml).

The above tests and data show that resveratrol can be administered to mammals as a prophylactic against chemically induced cancers.

What is claimed is:

1. A method for treating an individual susceptible to or afflicted with a skin condition, disorder or disease selected from the groups consisting of psoriasis, contact dermatitis, atopic dermatitis, actinic keratosis, a keratinization disorder, an epidermolysis bullosa disease, exfoliative dermatitis, seborrheic dermatitis, erythema multiforme, erythema nodosum, discoid lupus erythematosus, and dermatomyositis, comprising administering to the susceptible or affected area of the individual's skin a therapeutically effective anti-inflammatory amount of a topical pharmaceutical formulation that comprises a topical carrier and an active agent selected from the group consisting of resveratrol, pharmacologically acceptable salts, esters, amides, prodrugs and analogs thereof, and combinations of any of the foregoing.

2. The method of claim 1, wherein the active agent is cis-resveratrol or a pharmacologically acceptable salt, ester, amide, prodrug or analog thereof.

3. The method of claim 2, wherein the active agent is cis-resveratrol.

4. The method of claim 2, wherein the active agent is a conjugate of cis-resveratrol and a mono- or di-saccharide.

5. The method of claim 4, wherein the active agent is cis-resveratrol glucoside.

6. The method of claim 1, wherein the active agent is trans-resveratrol or a pharmacologically acceptable salt, ester, amide, prodrug or analog thereof.

7. The method of claim 6, wherein the active agent is trans-resveratrol.

8. The method of claim 6, wherein the active agent is a conjugate of trans-resveratrol and a mono- or di-saccharide.

9. The method of claim 8, wherein the active agent is trans-resveratrol glucoside.

10. The method of claim 1, wherein the active agent comprises a mixture of cis-resveratrol and trans-resveratrol.

11. The method of claim 1, wherein the topical pharmaceutical formulation comprises an ointment, lotion, cream, emulsion, microemulsion, gel or solution.

12. The method of claim 1, wherein the topical pharmaceutical formulation contains approximately 0.25 wt. % to 75 wt. % active agent.

13. The method of claim 12, wherein the topical pharmaceutical formulation contains approximately 0.25 wt. % to 30 wt. % active agent.

14. The method of claim 13, wherein the topical pharmaceutical formulation contains approximately 0.5 wt. % to 15 wt. % active agent.

15. The method of claim 14, wherein the topical pharmaceutical formulation contains approximately 1.0 wt. % to 10 wt. % active agent.

16. The method of claim 1, wherein the topical pharmaceutical formulation is administered at least once daily.

17. The method of claim 16, wherein the topical pharmaceutical formulation is administered one to four times daily.

18. A method for preventing or treating an individual susceptible to or afflicted with a skin condition, disorder or disease selected from the group consisting of psoriasis, contact dermatitis, atopic dermatitis, actinic keratosis, a keratinization disorder, an epidermolysis bullosa disease, exfoliative dermatitis, seborrheic dermatitis, erythema multiforme, erythema nodosum, discoid lupus erythematosus, and dermatomyositis, comprising administering to a susceptible or affected individual a pharmaceutical formulation comprised of an isotropically clear dispersion containing a therapeutically effective anti-inflammatory amount of an active agent selected from the group consisting of resveratrol, pharmacologically acceptable salts, esters, amides, prodrugs and analogs thereof, and combinations of any of the foregoing.

19. The method of claim 18, wherein the active agent is cis-resveratrol or a pharmacologically acceptable salt, ester, amide, prodrug or analog thereof.

20. The method of claim 19, wherein the active agent is cis-resveratrol.

21. The method of claim 19, wherein the active agent is a conjugate of cis-resveratrol and a mono- or di-saccharide.

22. The method of claim 21, wherein the active agent is cis-resveratrol glucoside.

23. The method of claim 18, wherein the active agent is trans-resveratrol or a pharmacologically acceptable salt, ester, amide, prodrug or analog thereof.

24. The method of claim 23, wherein the active agent is trans-resveratrol.

25. The method of claim 23, wherein the active agent is a conjugate of trans-resveratrol and a mono- or di-saccharide.

26. The method of claim 25, wherein the active agent is trans-resveratrol glucoside.

27. The method of claim 18, wherein the active agent comprises a mixture of cis-resveratrol and trans-resveratrol.

28. The method of claim 18, wherein the formulation comprises approximately 0.25 wt. % to 75 wt. % active agent.

29. The method of claim 28, wherein the formulation comprises approximately 0.25 wt. % to 30 wt. % active agent.

30. The method of claim 29, wherein the formulation comprises approximately 0.5 wt. % to 15 wt. % active agent.

31. The method of claim 30, wherein formulation comprises approximately 1.0 wt. % to 10 wt. % active agent.

32. The method of claim 18, wherein the topical pharmaceutical formulation is administered at least once daily.

33. The method of claim 32, wherein the topical pharmaceutical formulation is administered one to four times daily.

34. The method of claim 18, wherein the formulation is administered orally.

35. The method of claim 18, wherein the formulation is administered parenterally.

36. The method of claim 18, wherein the formulation is administered at least once daily.

37. The method of claim 36, wherein the formulation is administered one to four times daily.

* * * * *